US00PP32426P2

(12) United States Plant Patent
Klemm et al.

(10) Patent No.: US PP32,426 P2
(45) Date of Patent: Nov. 3, 2020

(54) ***DIANTHUS* PLANT NAMED 'KLEDG19308'**

(50) Latin Name: ***Dianthus* sp.**
Varietal Denomination: KLEDG19308

(71) Applicant: Klemm+Sohn GmbH & Co. KG, Stuttgart (DE)

(72) Inventors: Nils Klemm, Stuttgart (DE); Lena Thiede, Bempflingen (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 16/873,299

(22) Filed: Mar. 12, 2020

Related U.S. Application Data

(60) Provisional application No. 62/973,661, filed on Oct. 17, 2019.

(51) Int. Cl.
*A01H 5/02* (2018.01)
*A01H 6/30* (2018.01)

(52) U.S. Cl.
USPC ..... Plt./272

(58) Field of Classification Search
USPC ..... Plt./272
See application file for complete search history.

*Primary Examiner* — Susan McCormick Ewoldt
(74) *Attorney, Agent, or Firm* — Weatherly IP Solutions, LLC; James Weatherly

(57) ABSTRACT

A new *Dianthus* plant named 'KLEDG19308' particularly distinguished by single flowers with a light pink flower color with a purple center, medium incisions of the margin of the petal and a light green leaf color, is disclosed.

1 Drawing Sheet

Genus and species: *Dianthus* sp.
Variety denomination: 'KLEDG19308'.

BACKGROUND OF VARIETY 'KLEDG19308'

The present invention comprises a new and distinct variety of *Dianthus*, botanically known as *Dianthus* sp. and hereinafter referred to by the variety name 'KLEDG19308'. 'KLEDG19308' is a selection that resulted from an open pollination of the proprietary female *Dianthus* line 'DSS-2013-0080' (unpatented) and the proprietary male *Dianthus* line 'DSS-2013-0078'.

In May of 2014, the proprietary female *Dianthus* line 'DSS-2013-0080' and the proprietary male *Dianthus* line 'DSS-2013-00078' were cross pollinated in Stuttgart, Germany and seeds were obtained. The seeds were sown and plants were grown for evaluation. A plant line was selected in June of 2015 in Stuttgart, Germany, and named 'KLEDG19308'. In September of 2015, 'KLEDG19308' was first vegetatively propagated by vegetative cuttings. 'KLEDG19308' was found to reproduce true to type in successive generations of asexual propagation via vegetative cuttings in Stuttgart, Germany and Latina, Italy.

SUMMARY OF VARIETY 'KLEDG19308'

The following are the most outstanding and distinguishing characteristics of this new variety when grown under normal horticultural practices in Latina, Italy.

1. Single flowers with a light pink flower color with a purple center;
2. Medium incisions of the margin of the petal; and
3. Light green leaf color.

DESCRIPTION OF THE PHOTOGRAPH

This new *Dianthus* plant is illustrated by the accompanying photograph which shows the overall plant habit of the variety 'KLEDG19308' grown in a pot. The photograph is of a 14-week-old plant in Stuttgart, Germany under greenhouse conditions in March 2017.

DESCRIPTION OF THE NEW VARIETY 'KLEDG19308'

The following detailed descriptions set forth the distinctive characteristics of 'KLEDG19308'. Data was collected on eight-month-old plants potted and cultivated in Stuttgart, Germany in March of 2017. Color references are to The R.H.S. Colour Chart of The Royal Horticultural Society of London (R.H.S.), $5^{th}$ edition.

Classification:
- *Family*.—Caryophyllaceae.
- *Species*.—*Dianthus* sp.
- *Common name*.—Pot carnation.

Parentage:
- *Female parent*.—The *Dianthus* 'DSS-2013-0080'(unpatented).
- *Male parent*.—The *Dianthus* 'DSS-2013-0078'(unpatented).

Propagation:
- *Propagation type*.—Vegetative stem cuttings.
- *Time to produce a rooted young plant*.—14 to 18 days.
- *Root description*.—Young roots: RHS 161D. Mature roots: RHS 199C.
- *Rooting habit*.—Lanceolate.

Plant description:
- *Form*.—Upright.
- *Height*.—15.0 cm to 18.0 cm.
- *Diameter or spread*.—20.0 cm to 23.0 cm.

Lateral branches:
- *Length*.—5.0 cm to 10.0 cm.
- *Diameter*.—2.0 cm.
- *Internode length*.—2.5 cm to 5.0 cm.

*Number of internodes per branch/stem.*—2 to 4.
*Node length.*—0.2 cm to 0.4 cm.
*Node diameter.*—0.2 cm to 0.4 cm.
*Texture.*—Smooth.
*Color.*—RHS 146 C.
*Branch/stem.*—Solid.

Foliage description:
*Arrangement.*—Opposite.
*Length.*—2.0 cm to 5.0 cm.
*Width.*—0.2 cm to 0.4 cm.
*Shape.*—Lanceolate.
*Apex.*—Acute.
*Base.*—Obtuse.
*Margin.*—Entire.
*Texture.*—Upper and lower surfaces: Smooth.
*Immature leaf color.*—Upper surface: RHS 146A. Lower surface: RHS 146B.
*Mature leaf color.*—Upper and lower surfaces: RHS 147A. Venation pattern: No venation.

Flower description:
*Flower type and habit.*—Single flower, bowl shaped.
*Fragrance.*—Present.
*Natural flowering season.*—Spring to Autumn.
*Position of flowers relative to the foliage.*—Moderately above.
*Number of flowers per spray.*—3 to 6.
*Flower longevity on the plant.*—14 to 16 days.

Flower buds:
*Length.*—1.5 cm to 2.0 cm.
*Diameter.*—0.3 cm to 0.5 cm.
*Shape.*—Elliptic.
*Color.*—RHS 147B.
*Extrusion of the styles at the bud stage.*—Absent.

Corolla:
*Quantity of petals and arrangement.*—5.
*Corolla height.*—0.8 cm to 1.2 cm.
*Petal length.*—2.8 cm to 3.2 cm.
*Petal width.*—1.0 cm to 1.3 cm.
*Petal shape.*—Spoon shaped.
*Petal apex.*—Obtuse.
*Petal base.*—Acute.
*Petal margin.*—Serrated.
*Depth of petal margin.*—Medium.
*Petal texture.*—Upper and lower surfaces: Smooth.
*Petal color.*—Immature: Upper surface: RHS 69A and center RHS 59B. Lower surface: RHS 69C. Mature: Upper surface: RHS 69A and center RHS 59B. Lower surface: RHS 69C.
*Calyx.*—Quantity of sepals and arrangement: Composed of 5 sepals. Shape: Campanulate. Calyx height: 1.8 cm to 2.2 cm. Calyx diameter (at the apex): 0.4 cm to 0.6 cm. Sepal texture: Upper and lower surfaces: Smooth. Sepal color: Upper surface: RHS 137A. Lower surface: RHS 137D.

Peduncles:
*Length.*—1.0 to 2.0 cm (last internode), whole stem 10.0 cm.
*Diameter.*—0.1 cm to 0.2 cm.
*Strength.*—Moderate.
*Texture.*—Smooth.
*Color.*—RHS 147A.

Reproductive organs:
*Stamens.*—Quantity per flower: Not observed. Filament length: Not observed. Filament color: Not observed. Anther length: Not observed. Anther diameter: Not observed. Anther color: Not observed. Pollen amount: None.
*Pistils.*—Quantity per flower: 2. Pistil length: Not observed. Style length: 1.0 cm to 2.0 cm. Style color: RHS 155D. Stigma shape: Filamentous. Stigma color: RHS 85C. Ovary size: 0.5 cm to 0.7 cm. Ovary shape: Oval. Ovary color: RHS 145C.

Fruit and seed set: Seed sometimes observed.

Disease and insect/pest resistance: No special observations were made.

COMPARISON OF 'KLEDG19308' WITH PARENTAL LINES AND KNOWN VARIETY

When 'KLEDG19308' is compared to the female parental line 'DSS-2013-0080' and the male parental line 'DSS-2013-0078', the following differences are noted in Table 1:

TABLE 1

Comparison with Parental and Commercial Line

| Trait or characteristic | 'KLEDG19308' | Female parent | Male Parent |
|---|---|---|---|
| Flower color | Light pink, purple center | Purple, dark star | Light purple |
| Depth of incisions of margin of petal | Medium | Very shallow | Very shallow |

When 'KLEDG19308' is compared to the commercial line 'KLEDG18305' (U.S. Plant Pat. No. 31,019), the following differences are noted in Table 2:

TABLE 2

Comparison with Similar Variety

| Trait or characteristic | 'KLEDG19308' | Commercial line: 'KLEDG18305' |
|---|---|---|
| Flower type | Single | Single |
| Flower color | Light pink, purple center | Pink with purple ring |
| Leaf colour | Light green | Dark green |

We claim:

1. A new and distinct variety of *Dianthus* plant named 'KLEDG19303' as shown and described herein.

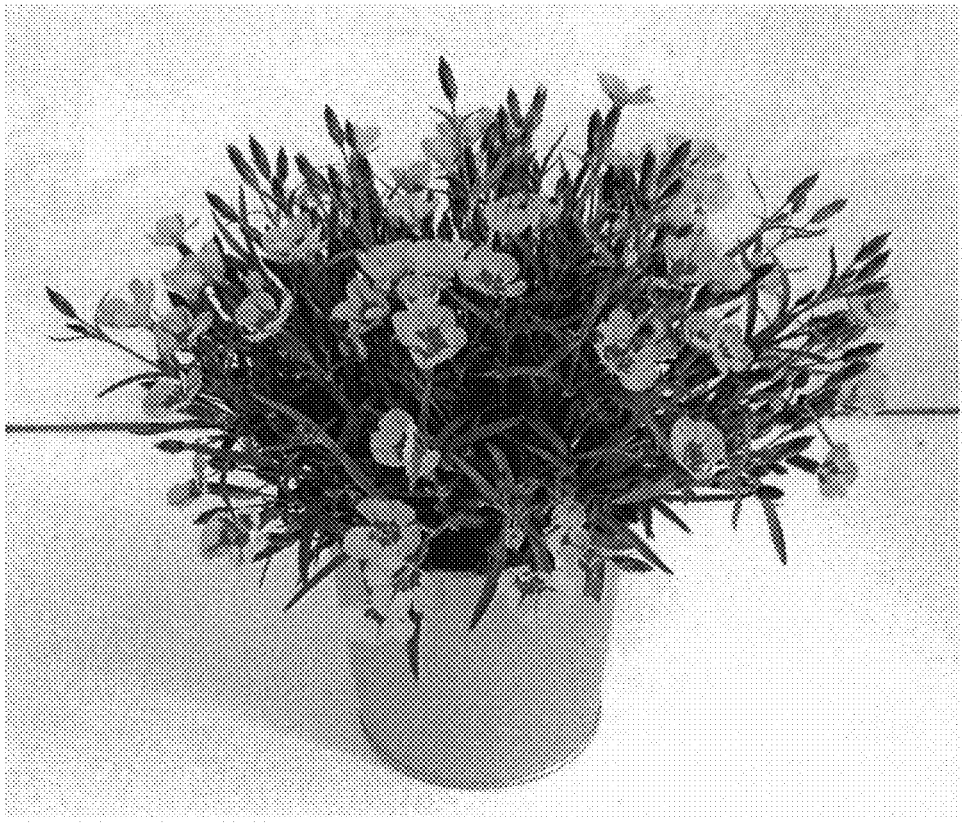

* * * * *